(12) United States Patent
Gaillot et al.

(10) Patent No.: US 11,529,467 B2
(45) Date of Patent: Dec. 20, 2022

(54) CONTAINER ADAPTER, DELIVERY ASSEMBLY AND METHOD OF DELIVERING A LIQUID TO A PATIENT

(71) Applicant: HOFFMANN-LA ROCHE INC., Little Falls, NJ (US)

(72) Inventors: Maxime Gaillot, Basel (CH); Roberta Leah, Basel (CH); Declan Reilly, Basel (CH); Paul Hayton, Bristol (GB); Jonathan Ridley, Bristol (GB)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 374 days.

(21) Appl. No.: 16/760,198

(22) PCT Filed: Nov. 2, 2018

(86) PCT No.: PCT/EP2018/079975
§ 371 (c)(1),
(2) Date: Apr. 29, 2020

(87) PCT Pub. No.: WO2019/086589
PCT Pub. Date: May 9, 2019

(65) Prior Publication Data
US 2021/0178070 A1     Jun. 17, 2021

(30) Foreign Application Priority Data

Nov. 2, 2017   (EP) ..................... 17199733

(51) Int. Cl.
*A61M 5/178*   (2006.01)
*A61J 1/20*    (2006.01)
*A61M 5/315*   (2006.01)

(52) U.S. Cl.
CPC .......... *A61M 5/1782* (2013.01); *A61J 1/2096* (2013.01); *A61M 5/31596* (2013.01)

(58) Field of Classification Search
CPC ............ A61M 5/1782; A61M 5/31596; A61M 2005/1787; A61J 1/2096; A61J 1/2003;
(Continued)

(56) References Cited

U.S. PATENT DOCUMENTS 4,507,113 A    3/1985  Dunlap
5,893,397 A *  4/1999  Peterson ............... A61J 1/2096
                                                     141/378

(Continued)

FOREIGN PATENT DOCUMENTS

EP    2857055 A1     4/2015
WO    2017102760 A1  6/2017

OTHER PUBLICATIONS

International Search Report dated Jan. 11, 2019 in PCT/EP2018/079975.

*Primary Examiner* — Bhisma Mehta
*Assistant Examiner* — Rachel T. Smith
(74) *Attorney, Agent, or Firm* — Medler Ferro Woodhouse & Mills PLLC (57) ABSTRACT

A container adapter for a medical delivery device is disclosed. The medical delivery device has a container seat for holding a container, a dosage chamber, a dosing mechanism and a lock mechanism adapted to prevent operation of the dosing mechanism when no container is held in the container seat and to allow operation of the dosing mechanism when the container is held in the container seat. The container adapter includes an adapter container seat arranged to hold a container, a joint structure arranged to be detachably positioned in the container seat of the medical delivery device and to connect the adapter container seat to the dosing mechanism, and an unlock member adapted to acti-
(Continued)

vate the lock mechanism. A delivery assembly and a method of delivering a liquid to a patient from different containers is also disclosed.

20 Claims, 8 Drawing Sheets

(58) Field of Classification Search
CPC ........ A61J 1/2006; A61J 1/201; A61J 1/2065; A65B 3/003
See application file for complete search history.

(56) References Cited

U.S. PATENT DOCUMENTS

| | | |
|---|---|---|
| 2003/0105430 A1 | 6/2003 | Lavi et al. |
| 2014/0261877 A1 | 9/2014 | Ivosevic et al. |

* cited by examiner

CONTAINER ADAPTER, DELIVERY ASSEMBLY AND METHOD OF DELIVERING A LIQUID TO A PATIENT

TECHNICAL FIELD

The present invention relates to a container adapter, a delivery assembly with a medical delivery device and such an adapter, and a delivery method using such a delivery assembly. Such systems and methods can be used for delivering a liquid stored in a container, such as a medicament or drug substance stored in a vial, in a definable dosage. For example, such delivery can be injection.

BACKGROUND ART

Delivering a liquid or other fluid out of a container is required in many medical applications and performed in a plurality of different ways. Particularly, where it is essential that the liquid is comparably precisely provided, specific devices are commonly used. For example, liquid pharmaceutical or drug substances are often provided in glass or plastic vials which are closed by a septum or rubber plug and a cap clamped around it or another similar seal cover.

Conventionally, for delivering the pharmaceutical substance out of vials, syringes can be used. Thereby, a transfer needle attached to a syringe penetrates the septum or cover and the pharmaceutical substance is withdrawn into the syringe through the transfer needle. Once transferred into the syringe, the pharmaceutical substance is delivered in an appropriate manner. For example, the substance can be, e.g. subcutaneously or intramuscularly, injected via an injection needle or it can be orally applied or provided as droplets, e.g., in the eyes or nose of the patient.

However, delivering liquids from vials or containers by means of syringes usually is comparably difficult. It typically makes it necessary that an educated person such as a doctor or a nurse is involved. In particular, in cases where the dosage of liquid delivered has to be comparably precise such as when comparable small volumes as in a range of ten microliter to about one milliliter are involved patients are typically not capable of performing the delivery themselves when using a syringe or a similar device.

For being able to provide the pharmaceutical or drug substances in containers or vials there exist devices which allow a particularly convenient and user friendly dosing. For example, in US 2003/0105430 A1 an automatic injection device having a barrel and an injection needle is described. A drug substance is provided in a vial closed by a vial stopper. For dosing the drug substance into the barrel, the vial is coupled to the injection device by means of an adapter. The drug substance is then closed into the barrel via the injection needle. In order that a contact between the injection needle and the vial stopper and, thus, a contamination of the injection needle is prevented the adapter can be equipped with a spike which pierces the vial stopper instead of the injection needle itself.

In another example, WO 2017/102760 A1 shows a delivery device having a vial seat for holding a vial in a predefined position, a dosage chamber, a dosing mechanism to transfer a liquid substance from the vial to the dosage chamber and a lock mechanism. For safety reasons, the lock mechanism is adapted to prevent operation of the dosing mechanism when no vial is held in the vial seat and to allow operation of the dosing mechanism when the vial is held in the vial seat. In use, the vial containing the drug substance to be administered is positioned in the vial seat. Thereby, a cap of the vial is pierced such that an interior of the vial is accessible. Also, the lock mechanism is activated such that the delivery device is free for dosing. By turning a dial unit of the delivery device with respect to a body part of the delivery device, the drug substance is withdrawn from the vial into the dosage chamber in a controlled and well definable manner. When an appropriate amount is dosed, the dial unit together with the vial is retracted from the body part and the drug substance is delivered from the dosage chamber, e.g., by injection.

However, a problem occurring in many pharmaceutical applications is that drug substances are not stable enough for being stored for an appropriate time. Or, they may require a comparably cumbersome handling or storage in order not to be affected before administration. Also, a specific composition of the drug substances may vary from one patient or application to the other. Therefore, some drug substances are provided in plural components which have to be mixed before administration. For example, it is known to provide components of a drug substance in plural vials. Before administration, the components are mixed, e.g., by transferring components from one vial to another by means of a syringe. Thereby, it typically is difficult to maintain hygienic or sterility standards and to ensure accurate handling.

Furthermore, in some applications it is desired to combine the content of different vials in order to prepare an appropriate dosage. In particular, vials of different fill volumes of a drug substance may be combined to achieve a specific dosage. This allows for providing the drug substance in smaller volumes such that wastage of the drug substance can be reduced. Particularly, when comparably costly drug substances are involved this may be beneficial.

Therefore, there is a need for a system or method allowing for a precise mixing and dosing of a multi component liquid provided in plural containers and for a convenient and secure self-administration.

DISCLOSURE OF THE INVENTION

According to the invention this need is settled by a container adapter as it is defined by the features of independent claim 1, by a delivery assembly as it is defined by the features of independent claim 10, and by a method as it is defined by the features of independent claim 15. Preferred embodiments are subject of the dependent claims.

In one aspect, the invention deals with a container adapter for a medical delivery device, such as the delivery device described in WO 2017/102760 A1, which has a container seat for holding a container in a predefined position, a dosage chamber, a dosing mechanism to transfer a liquid from the container held in the container seat to the dosage chamber and a lock mechanism adapted to prevent operation of the dosing mechanism when no container is held in the container seat and to allow operation of the dosing mechanism when the container is held in the container seat. The container adapter comprises an adapter container seat arranged to hold a container in a predefined position and a joint structure arranged or configured to be detachably positioned in the container seat of the medical delivery device and to connect the adapter container seat to the dosing mechanism of the medical delivery device when the joint structure is positioned in the container seat of the medical delivery device. The container adapter is particularly further equipped with an unlock member adapted or configured to activate the lock mechanism of the medical delivery device such that operation of the dosing mechanism is allowed when the joint structure of the container adapter is positioned in the container seat of the medical delivery device.

The medical delivery device can be a device for administering a liquid substance. For example, it can be a drug delivery device for applying a liquid medicament or drug substance. With such delivery devices the liquid substance or drug substance can be delivered or administered in an appropriate form such as by droplets for the eye, by oral dosages or the like. In particular, the medical delivery device can be an injection device for subcutaneously or intramuscularly injecting the drug substance.

The medical delivery device typically has a delivery orifice that can be shaped for a particular application or administration of the substance or medicament to be delivered. It can be a needle if, for example, the medical delivery device is intended for injecting the medicament. In such an embodiment the delivery orifice or needle can extend from the interior of a housing through its proximal opening out of the housing or a specific part thereof. The delivery orifice can also be adapted for being connected to a delivery member. For example, it can comprise a male or female part of a Luer lock or Luer taper connector and the delivery member can be equipped with a corresponding female or male Luer lock connector. Other examples of delivery orifices are nozzles, valves, fluid guides or the like.

The term "container" as used herein can relate to any liquid reservoir suitable for storing and transporting a liquid, other fluid, powder such as a lyophilized substance or capsules. Where the liquids, fluids or powders are drug substances or components thereof or the like, the container can particularly be a vial. The term "vial" as used in this connection can relate to a comparably small vessel or bottle, commonly used to store pharmaceutical substances or pharmaceuticals or medicaments in liquid, powdered or capsuled form. The vial can be made of a sterilisable material such as glass or plastic such as, e.g., polypropylene. The container can also comprise plural sub-containers such as plural vials. The term "predefined position" in this context can be such that an opening of the container is oriented towards the delivery orifice. Such a container seat allows for connecting a container at a well predefined position and orientation. This allows for efficiently coupling a container to the system or medical delivery device.

The term "drug" as used herein relates to a therapeutically active agent, also commonly called active pharmaceutical ingredient (API), as well as to a combination of plural such therapeutically active substances. The term also encompasses diagnostic or imaging agents, like for example contrast agents (e.g. MRI contrast agents), tracers (e.g. PET tracers) and hormones, that need to be administered in liquid form to the patient.

The term "drug substance", "pharmaceutical substance" or "pharmaceutical" as used herein relates to a drug as defined above formulated or reconstituted in a form that is suitable for administration to the patient. For example, besides the drug, a drug substance may additionally comprise an excipient and/or other auxiliary ingredients. A particularly preferred drug substance in the context of the invention is a drug solution, in particular a solution for oral administration, injection or infusion.

The term "drug product" as used herein or similar relates to a finished end product comprising a drug substance or a plurality of drug substances. In particular, a drug product may be a ready to use product having the drug substance in an appropriate dosage and/or in an appropriate form for administration. For example, a drug product may include an administration device such as a prefilled syringe or the like.

In order to be detachably positionable in the container seat of the medical delivery device, the joint structure is arranged appropriately. Thereby, it can have a similar or identical form as the container seat of the medical delivery device. Like this, it can receive and hold the container in the same specific manner as the medical delivery device. As the skilled person is aware, container seats of medical delivery devices can be configured in many ways to hold the container in the predefined position. In particular, they typically are adjusted to the shape or design of the specific container they are to be used for. For example, the container seats can be configured with a snap mechanism, e.g. having flexible arms and/or protrusions, to grab a neck of the container, with clamp mechanism for clamping a body of the container, with a sleeve to house and guide the container, or the like. Accordingly, the joint structure of the medical delivery device is arranged to be held by these means of the medical delivery device it is intended to be used with. For example, it can have a section formed in correspondence with a section of the container The container adapter can be made of a plastic material. In particular, it can be made of a sterilisable plastic material which can be manufactured in an injection molding process. It can be essentially cylindrically shaped. Also, it can be part of or integrated in another device.

The container adapter according to the invention allows for providing a, particularly liquid, substance from a container into the dosage chamber of the medical delivery device, and to remove the container from the medical delivery device wherein after removal the medical deliver device is ready for receiving a further container or a further container adapter in its container seat. Like this, substances from plural containers can be mixed either in the dosage chamber or in the further container. Thus, by means of the container adapter it can be achieved that plural substances are mixed in a comparably short time before delivery or administration. This makes it possible, that components of a drug substance each are provided in a preferred and advantageous manner and that the drug substance to be delivered is generated shortly before administration. For example, components of a drug substance which cannot stably be stored or stored under the same conditions can be combined shortly before administration. Also, different drug substances can be mixed before administration or an appropriate dosage of a drug substance can be withdrawn from two or more containers.

The unlock member can have any form or shape suitable for interacting with the lock mechanism of the medical delivery device. In particular, the lock mechanism of the medical delivery device can be embodied in many different ways. Thereby, typically it is equipped with a structure to be pushed, moved, pressed or otherwise activated to release the locking and to allow operation of the dosing mechanism. Thus, the unlock member of the container adapter is designed corresponding to this structure such that the unlock mechanism is activated when the joint structure of the container adapter is positioned in the container seat of the medical delivery device. For many advantageous applications, it preferably comprises an abutting surface arranged to contact a push portion of the lock mechanism of the medical delivery device when the container adapter is forwarded into the container seat of the medical delivery device such that the push portion of the lock mechanism is axially displaced when the container adapter is attached to the medical delivery device. By such displacement, the lock mechanism can be activated such that the medical delivery device is brought in an unlocked state. In such unlocked state, the medical delivery device can be operated to dose an amount of liquid from the container to a dosage chamber.

Preferably, the unlock member comprises an engaging surface arranged to engage behind a pull portion of the lock mechanism of the medical delivery device when the container adapter is forwarded into the container seat of the medical delivery device such that the pull portion of the lock mechanism is axially displaced when the container adapter is retracted from the medical delivery device. Such reverse displacement allows to put the lock mechanism back in its initial state in which the operation or dosing of the medical delivery device is blocked or prevented. Like this, the medical delivery device can be switched back to the locked state when the container adapter is removed after dosing. In a preferred embodiment, the push portion and the pull portion of the lock mechanism of the medical delivery device are stationary to each other such as embodied in one physical unit or piece. They can be embodied by appropriate surfaces which can essentially face away from each other.

The adapter container seat of the container adapter can have any suitable form or shape for receiving and/or holding the container in the predefined position. The predefined position can particularly be an arrangement in which the container is oriented such that an opening thereof, which typically is covered by a cap, faces the medical delivery device when the container adapter is positioned in the container seat of the medical delivery device. For example, the adapter container seat can be equipped with a retainer shaped in correspondence with a portion of the container having its opening such as a head portion thereof or the like. Such retainer can efficiently be arranged in order that the container is in the predefined position.

Preferably, the adapter container seat has a fixation structure adapted to irremovably hold the container in the predefined position. Such fixation structure allows for preventing that the container is unintentionally or inappropriately removed from the container adapter, e.g. during or after dosing. Thereby, the fixation structure of the adapter container seat preferably has a clip arranged to snap behind a head portion of the container when the container is held in the adapter container seat. Such clip can be an easy and reliable constructive realization of the fixation structure.

When the container adapter is mounted to the medial delivery device it can be important that no unintended contact with specific members of the medical delivery device occurs. For example such unintended contact may cause the medical delivery device to be brought in an unlock status or to affect means for fixing a container or the like. For that purpose it may be crucial that the container adapter is mounted in a specific orientation such as a particular rotational position. To ensure this, the container adapter preferably comprises an alignment formation arranged to assure that the container adapter is in a predefined orientation relative to the medical delivery device when the joint structure is positioned in the container seat of the medical delivery device.

Preferably, the joint structure of the container adapter is arranged to form a open tight duct between an interior of the container and the dosing mechanism of the medical delivery device when the container is held in the adapter container seat and the joint structure is positioned in the container seat of the medical delivery device. Such open tight duct allows the dosing mechanism to efficiently access the drug substance or component stored in the container during dosing. In particular, the open tight duct allows for efficiently transferring a liquid drug or substance from the container into the dosage chamber of the medical delivery device when the adapter is mounted to the medical delivery device and the container is arranged in the container seat.

As used herein, the term "cap" can relate to any cover suitable for closing an opening of the container. For example, such cap can be or comprise a septum or rubber stopper forwarded in the opening of the container. It can further comprise a metal or plastic cover which is arranged or crimped around the opening and the septum or stopper. The cover can hold and protect the septum or stopper. When penetrating such septum, stopper or cap of the container the needle of the medical deliver device may get contaminated. However, such contaminations are undesired in many applications such as, e.g., when injections are involved. Furthermore, often a considerable amount of air may be withdrawn into the dosing chamber of the medical delivery device before the liquid substance when dosing happens via the needle. Such air in the syringe typically has to be eliminated out of the syringe before applying the substance in a priming step. However, priming steps can make it difficult to dose and deliver a precise amount of liquid particularly when the amount of liquid is comparably small such as in a range of about 10 μl to 1 ml.

For achieving a better situation in this connection, the adapter container seat preferably comprises a spike arranged to penetrate a cap of an opening of the container when the container is held in the adapter container seat. By means of such spike, it can particularly be prevented that the delivery orifice or needle itself has to penetrate the cap. This allows for reducing the risk of harming or contaminating the delivery orifice of the medical delivery device. For example, when the cap comprises a septum, it can be prevented that the delivery orifice has to be pierced through the septum which typically contaminates or desiliconizes the delivery orifice and which also can damage the delivery orifice or its tip. Thus, the spike allows keeping the delivery orifice in a condition ready for administration such as for injection or the like. Like this, the adapter allows for delivering a precise dosage of a liquid in a closed system.

Thereby, the spike of the adapter container seat preferably extends in the interior of the adapter container seat. Such an arrangement of the spike allows for directly penetrating the cap of the container when it is arranged or placed in the adapter container seat. Thereby it can be advantageous when the adapter container seat is arranged for holding the container with its opening directed towards the spike.

Preferably, the spike comprises a tip. The tip can be embodied sharp enough to pierce and penetrate the cap or its septum or stopper. Such a spike allows for conveniently penetrating the cap in an appropriate way. Thereby, the spike preferably comprises a conduit which runs from the tip longitudinally through the spike. The term "longitudinal" in this connection can relate to a direction of the spike. In particular, the spike can be oriented along an axis of the container. The conduit of the spike allows for ultimately connecting the container to the delivery orifice and to transfer a liquid from the container to the delivery orifice or dosage chamber.

Preferably, the container adapter comprises a seal which seals the container seat of the medical delivery device to the joint structure when the joint structure is positioned in the container seat of the medical delivery device. Such an arrangement allows for minimizing an air volume around the medical delivery device and ensure tightness between the container adapter and the medical delivery device. Advantageously, the seal is located as close to the tip or proximal end of the delivery orifice or medical delivery device as possible. By means of the seal it can be achieved that the delivery orifice is protected and contamination is reduced or prevented. Also, the seal can prevent spillage of the liquid or drug substance when the adapter is not attached to the medical delivery device.

The joint structure of the container adapter preferably comprises a seal holder in which the seal is tightly arranged. For example, such a seal holder can be embodied as a recess which fits the seal. The seal can then be slightly compressed and pushed inside the recess such that it is held by friction in the recess.

Another aspect of the invention relates to a delivery assembly having a container adapter as described above and a medical delivery device. The medical delivery device comprises a container seat for holding a container in a predefined position, a dosage chamber, a dosing mechanism to transfer a liquid from the container held in the container seat to the dosage chamber and a lock mechanism adapted to prevent operation of the dosing mechanism when no container is held in the container seat and to allow operation of the dosing mechanism when the container is held in the container seat.

By means of such a delivery assembly and its preferred embodiments described below the effects and benefits of the container adapter according to the invention and its preferred embodiments can efficiently be achieved.

Thereby, the container seat of the medical delivery device preferably has a fixation structure adapted to irremovably hold a container in a predefined position and the joint structure of the container adapter is arranged to prevent interaction with the fixation structure of the container seat of the medical delivery device, when the container adapter is held in the container seat of the medical delivery device. For example, the joint structure can be formed with an at least in one orientation reduced diameter compared to a container in order to prevent interaction. Such an arrangement allows for mounting the container adapter to the medical delivery device without being fixed by the latter. Like this it can be achieved, that the container adapter is retracted or removed from the medical delivery device after dosing and that the medical delivery device is ready for receiving a further container or a further container adapter.

Preferably, the lock mechanism of the medical delivery device comprises a push portion and the unlock member of the container adapter comprises an abutting surface, the push portion of the lock mechanism and the abutting surface of the unlock member being arranged to interact when the container adapter is forwarded into the container seat of the medical delivery device such that the push portion of the lock mechanism is axially displaced when the container adapter is attached to the medical delivery device. In particular, the abutting surface can push the push portion into the medical delivery device or towards a distal end of the medical delivery device, respectively. Such arrangement allows for efficiently and automatically unlocking the medical delivery device when positioning the joint structure of the container adapter in the container seat of the medical delivery device.

Preferably, the lock mechanism of the medical delivery device comprises a pull portion and the unlock member of the container adapter comprises an engaging surface, the pull portion of the lock mechanism and the engaging surface of the unlock member being arranged to inter-engage when the container adapter is forwarded into the container seat of the medical delivery device such that the pull portion of the lock mechanism is axially displaced when the container adapter is retracted from the medical delivery device. In particular, the unlock member can pull the lock mechanism when the container adapter is detached. Such arrangement allows for efficiently and automatically relocking the medical delivery device when removing or retracting the container adapter from the medical delivery device.

As mentioned above in connection with the container adapter, the medical delivery device preferably comprises a delivery orifice such as a needle or needle adapter for delivering a substance and the container adapter comprises a conduit ending at the adapter container seat, and the delivery orifice of the medical delivery device extends into the conduit of the container seat when the container adapter is held in the container seat of the medical delivery device. Thereby, the delivery assembly preferably comprises a delivery orifice seal arranged to tightly abut the adapter container seat of the container adapter at a side where the conduit ends. Also, the delivery orifice seal preferably is shaped as a plug, preferably made of an elastomer or a silicone.

Preferably, the delivery assembly comprises a securing element, wherein the container seat of the medical delivery device is decouplably mounted to a delivery orifice of the medical delivery device and the securing element is arranged for preventing unintended decoupling of the container seat from the delivery orifice when the container adapter is retracted from the medical delivery device. Such a securing element allows for preventing that, upon removal or retraction of the container adapter, the container seat or a portion of the medical delivery device comprising the container seat is decoupled from the delivery orifice. Like this, it can be prevented that the delivery orifice is exposed before the drug substance is ready, i.e. all components thereof are mixed.

Thereby, the securing element preferably is a sheet piece having an adhering surface. Such sheet piece may be positioned or adhered over borders of the medical delivery device to be held together. When the drug substance is finally prepared or mixed, the sheet piece can be removed and the delivery orifice can be exposed.

Another further aspect of the invention relates to a method of delivering a liquid to a patient. The method comprises the steps of: obtaining a first container with a liquid first mixing substance, a second container with a second mixing substance and a delivery assembly as described above; arranging the first container in an adapter container seat of a container adapter of the delivery assembly; positioning a joint structure of the container adapter of the delivery assembly in a container seat of a medical delivery device of the delivery assembly; withdrawing the first substance from the first container into a dosage chamber of the medical delivery device of the delivery assembly; retracting the container adapter of the delivery assembly from the medical delivery device of the delivery assembly; positioning the second container in the container seat of the medical delivery device of the delivery assembly; and withdrawing the second substance from the second container into the dosage chamber of the medical delivery device of the delivery assembly.

The first and second mixing substances can be substances which have to be combined or mixed for resulting a final substance to be administered by the medical delivery device. In particular, they can be components which can be mixed or combined such that a drug substance results which is to be administered. The first and second mixing substances can also be the same substances which are combined to achieve an appropriate dosage of it. The method can also involve dosing of further mixing substances stored in further containers via further container adapters.

The steps of the method can also be embodied in another sequence than listed herein before. The method according to the invention and its preferred embodiments allow to efficiently achieve the effects and benefits described above in connection with the delivery assembly and its preferred embodiments.

Preferably, the method comprises the step of forwarding the first mixing substance into the second container when the second container is positioned in the container seat of the medical delivery device of the delivery assembly. Such arrangement allows for mixing the first and second substances in the second container before withdrawing the second substance from the second container. For example, this allows for providing the second substance in a dry form, such as in the form of a lyophilized powder or the like, and reconstituting the second substance inside the second container before withdrawal or dosing into the medical delivery device.

BRIEF DESCRIPTION OF THE DRAWINGS

The container adapter, the delivery assembly and the method according to the invention are described in more detail herein below by way of an exemplary embodiment and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes includes various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
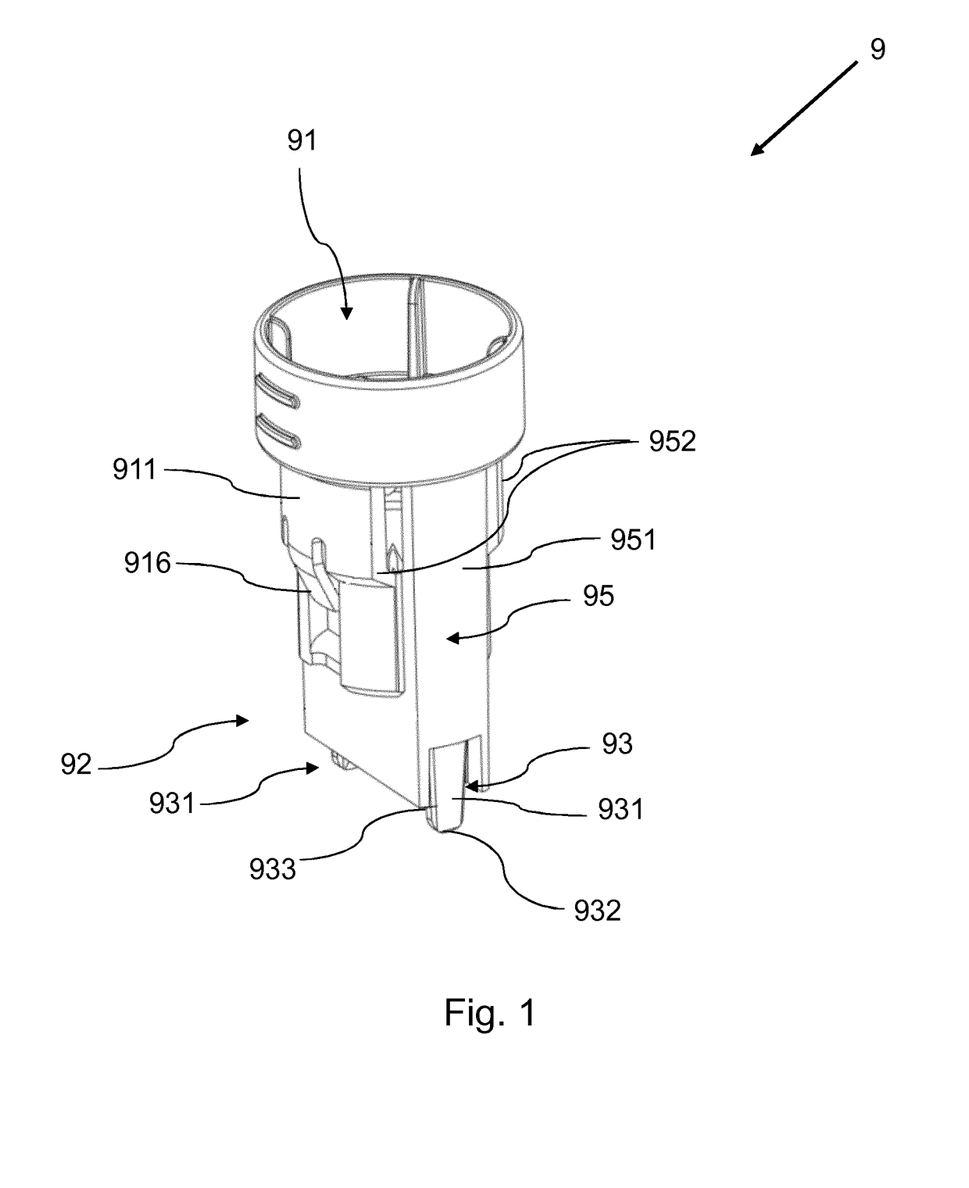
FIG. 1 shows a perspective view of an embodiment of a container adapter for a medical delivery device according to the present invention.
Figure 2:
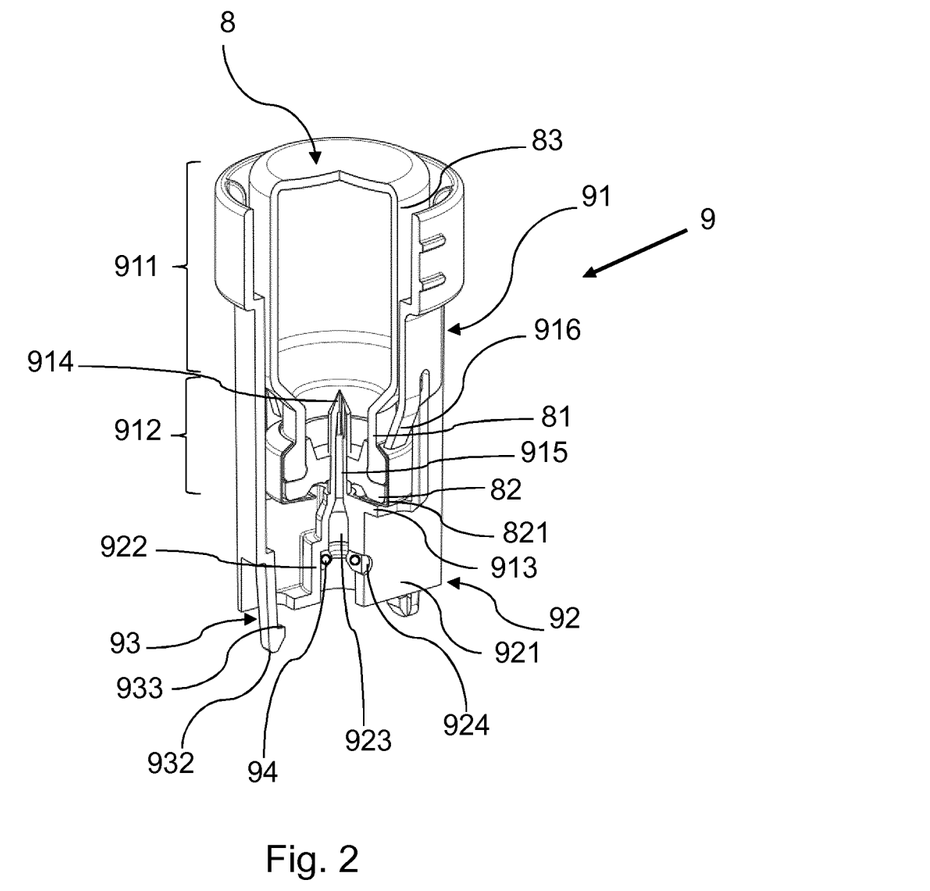
FIG. 2 shows a section view of the container adapter of FIG. 1, wherein a first container has been lodged in a predefined position within an adapter container seat.

FIG. 1 shows a container adapter 9 for a medical delivery device 1 according to the present invention. With reference to FIGS. 1, 2, 3 and 7, the container adapter 9 is configured to be held in a container seat 53 of the medical delivery device 1 and comprises an adapter container seat 91 and a joint structure 92. The adapter container seat 91 is arranged to hold a container 8, namely a vial in the specific case, in a predefined position. The joint structure 92 is arranged to be detachably positioned in the container seat 53 of the medical delivery device 1. The joint structure 92 is formed with an in particular orientations reduced diameter with respect to that of container 8, so that any interference and adverse interaction with a fixation structure of the container seat 53 is prevented. Moreover, the joint structure 92 is arranged so that, when it has been positioned in the container seat 53, it connects the adapter container seat 91 to a dosing mechanism adapted to transfer liquid from the container 8 held in the container seat 53 to a dosage chamber 61 of the medical delivery device 1.

A lock mechanism of the medical delivery device is adapted to prevent operation of the dosing mechanism when no container 8 is held in the container seat 53 and to allow operation of the dosing mechanism when the container 8 is held in the container seat 53.

An unlock member 93 of the container adapter 9 is adapted to activate the lock mechanism of the medical delivery device 1 such that operation of the dosing mechanism is allowed when the joint structure 92 is positioned in the container seat 53 of the medical delivery device 1.

The container adapter 9 allows for providing a, particularly liquid, substance from a container 8 into the dosage chamber 61 of the medical delivery device 1, and to remove the container adapter 9 together with the container 8 from the medical delivery device 1 wherein, after removal, the medical deliver device 1 is ready for receiving a further, different container 8 or a further container adapter 9 in its container seat 53. Like this, substances from plural containers 8 can be mixed either in the dosage chamber 61 or in any of the further containers 8. Thus, by means of the container adapter 9, it can be achieved that plural substances are mixed in a comparably short time before delivery or administration. This makes it possible that components of a drug substance are each provided in a preferred and advantageous manner, and that the drug substance is generated shortly before administration.

The container adapter 9 comprises a sleeve portion 921 as part of the joint structure 92 interfacing with the container seat 53 of the device 1. A head holding portion 912 is adapted to receive and secure the head portion or cap 82 of the container 8. A body support portion 911 is arranged to enfold and carry a body 83 of the container 8.

To better illustrate the cooperation of the container adapter's joint structure 92 with the lock mechanism of the medical delivery device 1, the components of the medical delivery device 1 will be in the following described in a more detailed way. As a reference for structural details, a medical delivery device similar to the one adopted in combination with the container adapter 9 of the present invention—although adapted and meant for delivery of liquid from one single container 8—is in WO 2017/102760 A1.

Figure 3:
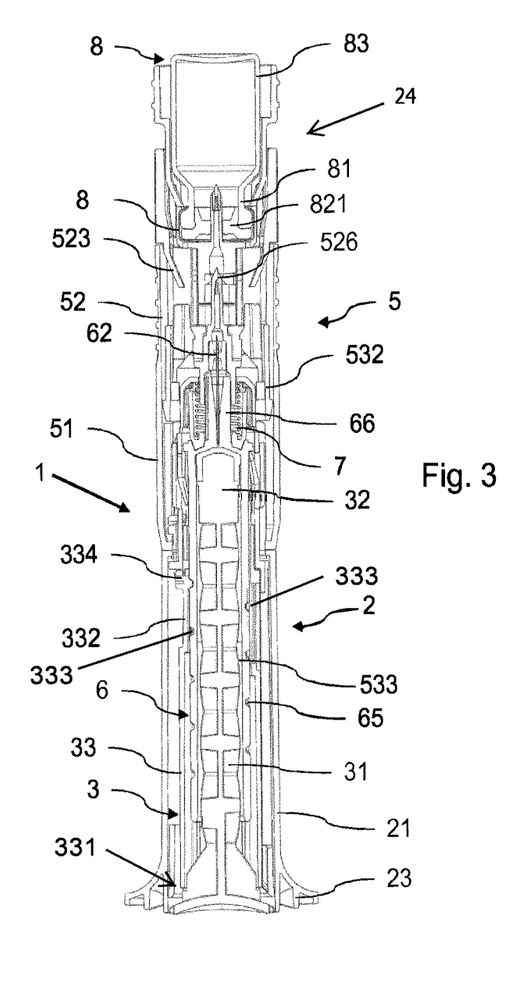
FIG. 3 shows a section view of the container adapter of FIG. 1, when being provided with a first container to be held in the adapter container seat and while being inserted in a container seat of a medical delivery device.
Figure 3A:
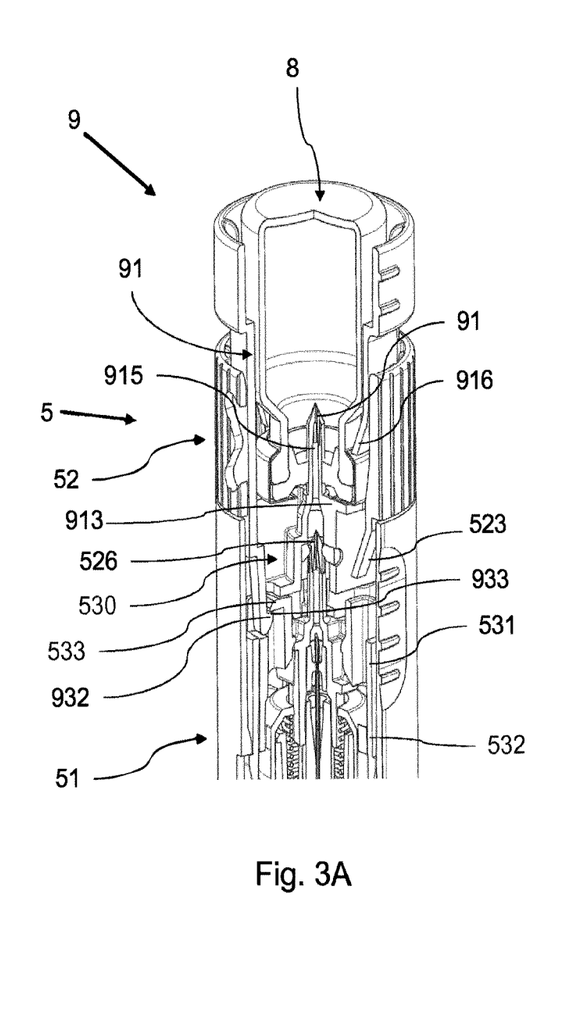
FIG. 3A shows a detail of a partially sectioned view of the medical delivery device of FIG. 3, particularly highlighting a connection of the adapter container seat with a dosing mechanism of the medical delivery device.

With reference to FIG. 3, the medical delivery device 1 comprises a dosing activator 5 and an injection device. The injection device has a housing 2 with a distal body section 21 passing over into a finger flange 23 at its lower or bottom end. The housing 2 has a hollow interior, a distal opening provided at the finger flange 23 and a proximal opening provided at a proximal end side 24 of the housing 2.

In the interior of the housing 2, a rod element 3 is arranged. On the upper portion of the housing 2, a sleeve unit 51 of the dosing activator 5 is arranged. The sleeve unit 51 is formed as a vertically extending hollow cylinder.

The sleeve unit 51 is connected to a rotatable dial unit 52 of the dosing activator 5. The dial unit 52 is essentially cylindrically shaped and vertically extends from the sleeve unit 51 in an upward direction. An outer surface of the dial unit 52 is equipped with gripping ribs for allowing a convenient manual operation. Furthermore, the dial unit 52 is equipped with a neck holder 523 having two snap-in arms.

The medical delivery device 1 is embodied to receive the vial 8 as container. In a common manner, the vial 8 has the body 83 and a neck 81 which is closed by a cap 82. In the interior of the body 83 a liquid drug substance is stored which is to deliver or inject by means of the injection device.

The rod element 3 comprises a hollow body portion 33 which coaxially extends to and, when mounted, surrounds a stem 31. The body portion 33 has arm sections 332 each of which at one end is fixed to the rest of the body portion 33 and at the other end has an outwardly extending release hump 334. Furthermore, each of the arm sections 332 is equipped with a pin 333 projecting towards the stem 31 in an essentially radial direction. At a distal end, the body portion 33 of the rod element 3 comprises four clip latches 331. To a proximal axial end of the stem 31, a rubber stopper 32 is mounted as shown in more detail below.

The dosage member 6 of the injection device comprises a hollow chamber cylinder 61 as chamber body. At an outer surface of the chamber cylinder 61, a thread 65 runs. Further, the outer surface 61 is provided with a dosage marking. The interior of the chamber cylinder 61 is dimensioned to receive the stem 31 and the rubber stopper 32 of the rod element 3. Thereby, the rubber stopper 32 is dimensioned to tightly fit into the interior of the chamber cylinder 61. At its proximal end the chamber cylinder 61 passes over into a male coupling structure 66 and, proximally projecting therefrom, a delivery needle 62, or orifice. Between the dosage member 6 and the housing 2, a spring 7 is positioned.

The body 2 is provided with a plurality of grooves at an outer circumference adjacent to its end side.

The release member 530 of the dosing activator 5 comprises a ring portion 531 of the release member 530; from the ring portion 531 two stems 532 axially extend into the proximal direction and blocking surfaces are formed at the inside of the ring portion 531.

In the inside of the dial unit 52 of the dosing activator 5, a female coupling structure extends into a distal direction. The female coupling structure is formed to fit a male coupling structure 66 of the dosage member 6. At its distal end, the dial unit 52 further has a sleeve mount structure onto which a dial mount of the sleeve unit 51 can be snapped. When being connected, the dial unit 52 can rotate but not axially move relative to each other.

The cap 82 of the container 8 is provided with a septum 821.

Inside the hollow interior of the dial unit 52 of the dosing activator 5, a vial seat 53 is formed which comprises the neck holder 523, a rest surface of the release member 530 and a spike 526 vertically extending from the top end of the female coupling structure. The blocking surfaces of the ring portion 531, in the form of stems 532, engage the grooves as corresponding surfaces at the proximal end side of the housing 2. Thereby, a rotational movement of dial unit 52 is prevented and the medical delivery device 1 is in a locked status, wherein operation of the dosing mechanism is prevented and no container 8 is positioned in the vial seat 53. Such a locked status is represented in FIG. 7A.

Figure 8:
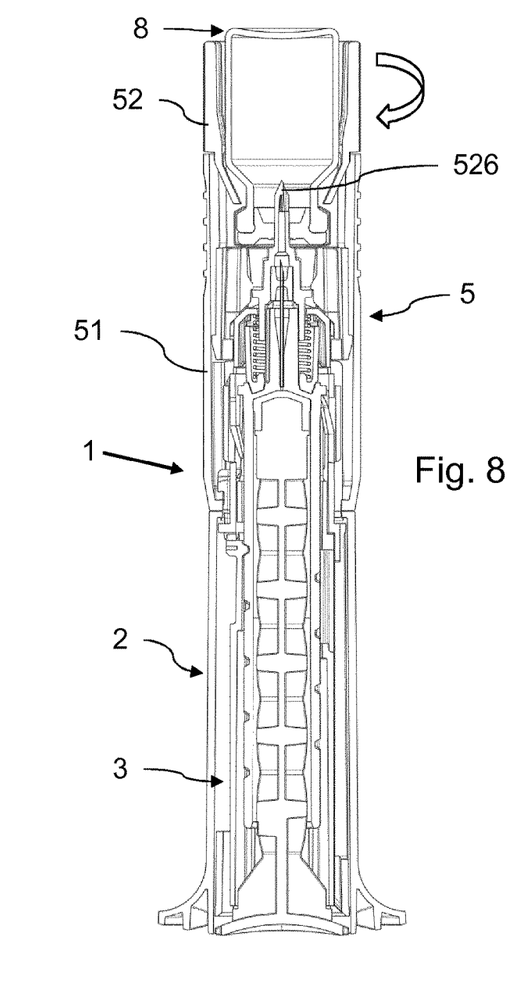
FIG. 8 shows a section view of the medical delivery device of FIG. 3, when the positioning of the second container in the container seat of the medical delivery device has brought the medical delivery device newly in an unlocked state wherein withdrawing of a second liquid from the second container into the dosage chamber is enabled by rotation of the dial of the dosing mechanism of the medical delivery device.
Figure 8A:
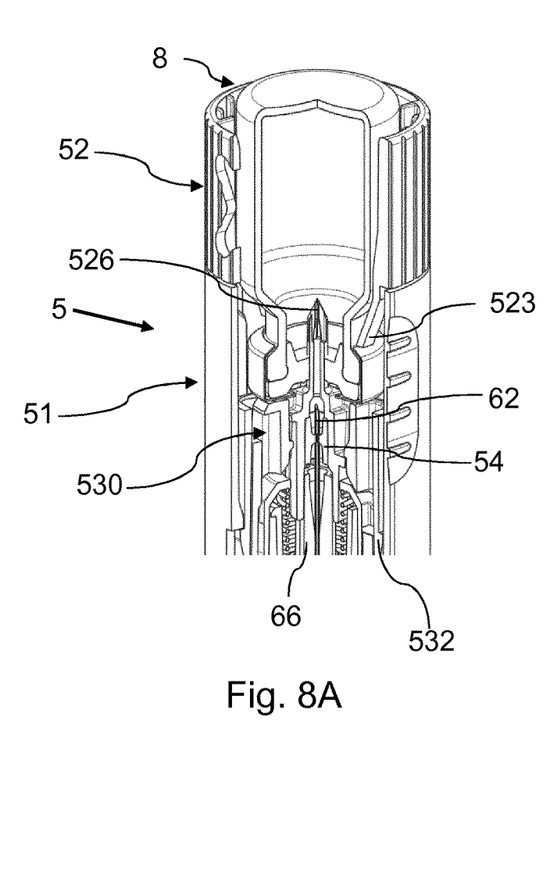
FIG. 8A shows a detail of a further partially sectioned view of the medical delivery device of FIG. 8, particularly representing a rotation of the dial of the dosing mechanism of the medical delivery device to withdraw liquid from the second container.

In FIG. 8 and FIG. 8A, the medical delivery device 1 is shown after being changed from the lock status to a dosing status. In a step of preparing the medical delivery device 1, the vial 8 is pressed top down into the dosing activator 5 and its vial seat 53. Thereby, vial 8 abuts the rest surface of the release member 530 and downwardly moves it until the blocking surfaces of the ring portion 531 disengage the grooves of the housing 2. Like this, the dial unit 52 is made rotatable in relation to the sleeve unit 51 and the housing 2 and the medical delivery device 1 is unlocked, i.e. in the dosing status. The blocking surfaces 532 of the release member 530 therefore disengage the corresponding surfaces of the medical delivery device 1 when the release member is made axially move as a result of the arrangement of a container 8 in the container seat 53.

When the vial 8 is downwardly pushed in the container seat 53, the retaining arms 523 of the neck holder are moved in an outward direction such that a head of the vial 8 with the cap 82 passes flange ends of the retaining arms 523. Once the vial 8 is sufficiently pressed down, the flange ends of the retaining arms 523 snap behind the head in the neck 81 of the vial 8, such that the vial 80 is safely held. In this way, the vial 8 is vertically mounted top down in the medical delivery device 1.

Furthermore, while the vial 8 is pressed into the vial seat, a tip of the spike 526 penetrates the cap 82 including the septum 821. Below the spike 526, a tip of the delivery needle 62 is arranged. The delivery needle 62 is partially covered by the needle seal 54. The delivery needle 62 extends from the spike 526 through the male coupling structure 66 of the chamber cylinder 61. Like this, in the dosing status shown in FIGS. 8 and 8A, the spike 526 together with the delivery needle 62 form an open duct as transfer channel between the interior of the vial 8 and the interior of the chamber cylinder, or chamber body or dosage chamber, 61 of the dosage member 6. Thereby, the needle seal 54 allows for eliminating leakage and minimizing the free space between the delivery needle 62 and the spike 526. In the dosing status, the pins 333 of the arm sections 332 of the rod element 3 engage the thread 65 of the dosage member 6.

As mentioned, the container adapter 9 according to the present invention is designed to cooperate with the locking mechanism of the medical delivery device 1 as above described. To this purpose, the unlock member 93 comprises an abutting surface 932 arranged to contact a push portion of the lock mechanism of the medical delivery device 1 when the container adapter 9 is forwarded into the container seat 53 of the medical delivery device 1. The push portion can be a part of the release member 530 of the lock mechanism, such as surfaces of the stems 532 incorporating the blocking surfaces above described. Upon the application of a load by the abutting surface 932, the push portion 532 of the lock mechanism, possibly integrally with the whole body of the release member 530, is axially displaced, in connection with the container adapter 9 being attached to the medical delivery device 1. By such displacement, the lock mechanism can be activated such that the medical delivery device 1 is brought in an unlocked state. In such unlocked state, the medical delivery device 1 can be operated to dose an amount of liquid from the container 8 lodged in the container adapter seat 91 to the dosage chamber 61.

At the same time, the unlock member 93 comprises an engaging surface 933 arranged to engage behind a pull portion 533 of the lock mechanism of the medical delivery device 1 when the container adapter 9 is forwarded into the container seat 53 of the medical delivery device 1. Thus, the pull portion 533 of the lock mechanism is axially displaced when the container adapter 9 is retracted from the medical delivery device 1. Such displacement allows to bring the lock mechanism back in its initial state in which the operation or dosing of the medical delivery device 1 is blocked or prevented. Like this, the medical delivery device 1 can be switched back to the locked state when the container adapter 9 is removed, after dosing.

The abutting surface 932 and the engaging surface 933 are, in the embodiment represented in FIG. 1, incorporated in an arm portion 931 acting as a lock clip for the dial 52.

The adapter container seat 91 has a fixation structure 916 adapted to irremovably hold the container 8 in the predefined position. Analogously to the dosing activator 5, this fixation structure can take the form of clips 916 arranged to snap behind a head portion or cap 82 of the container 8, when the container 8 is held in the adapter seat 91.

To ensure that the container adapter 9 is secured in a predefined orientation relative to the medical delivery device 1 when the joint structure 92 is positioned in the container seat 53 of the medical delivery device 1, the container adapter is provided with an alignment formation 95. Such alignment formation can take the form of an alignment surface 951 designed to engage a corresponding guide groove or rail of the delivery device 1 and/or of male projections 952 configured to fit corresponding female notches or channels of the delivery device 1. At any rate, the alignment formation can be any anti-rotational feature which, in cooperation with matching features of the medical delivery device 1, prevents a rotational displacement, or more generally a change in orientation, of the container adapter 9 within the container seat 53 during operation.

The joint structure 92 is arranged to form an open duct between an interior of the container 8 and the dosing mechanism of the medical delivery device 1 when the container 8 is held in the adapter container seat 91 and the joint structure 92 is positioned in the container seat 53 of the medical delivery device 1. Such open duct can take the form of a channel 923 receiving the spike 526 of the medical delivery device 1. The open duct is formed within a central post 922.

The adapter container seat 91 comprises a spike 914 arranged to penetrate a cap 82 of an opening of the container 8 when the container 8 is held in the adapter container seat 91. The spike 914 extends from a base plate 913 in the interior of the adapter container seat 91 and comprises a tip. The adapter container seat 91 comprises a conduit 915 which runs from the tip longitudinally through the spike 914. Thus, the conduit 915 establishes a fluid communication between the interior of the container 8 to the channel 923 of the joint structure 92 receiving the spike 526 of the device 1. The spike 516, as part of the container seat 53 of the device 1, extends into the channel 923 leading to conduit 915. This configuration, as well as the provision of a seal as below explained, allows for a tight connection between the container seat 52 of the device 1 and the container adapter 9.

A seal 94 seals the container seat 53 of the medical delivery device 1 to the joint structure 92, when the joint structure 92 is positioned in the container seat 53 of the medical delivery device 1. Thus, it is guaranteed that the liquid from the container 8 lodged in the container adapter 9 is entirely transferred through the spike 526 to the dosage chamber 61 of the device 1. The joint structure 92 comprises further a seal holder 924 in which the seal 94 is tightly arranged.

The container adapter 9 and the medical device, coupled as above described and as shown in FIGS. 4, 4A, 5 and 5A, form a delivery assembly.

Figure 4:
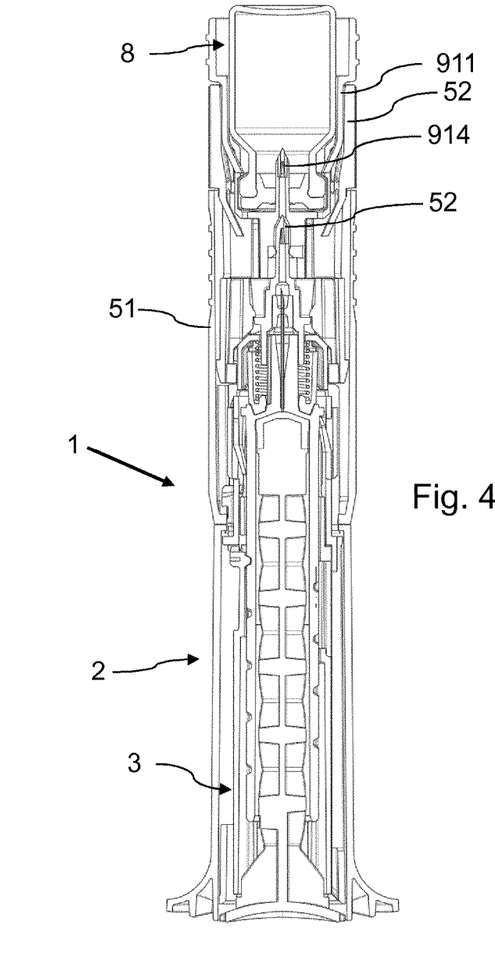
FIG. 4 shows a section view of the medical delivery device of FIG. 3, when the container adapter has been forwarded into the container seat of the medical delivery device, to activate a lock mechanism of the medical delivery device.
Figure 4A:
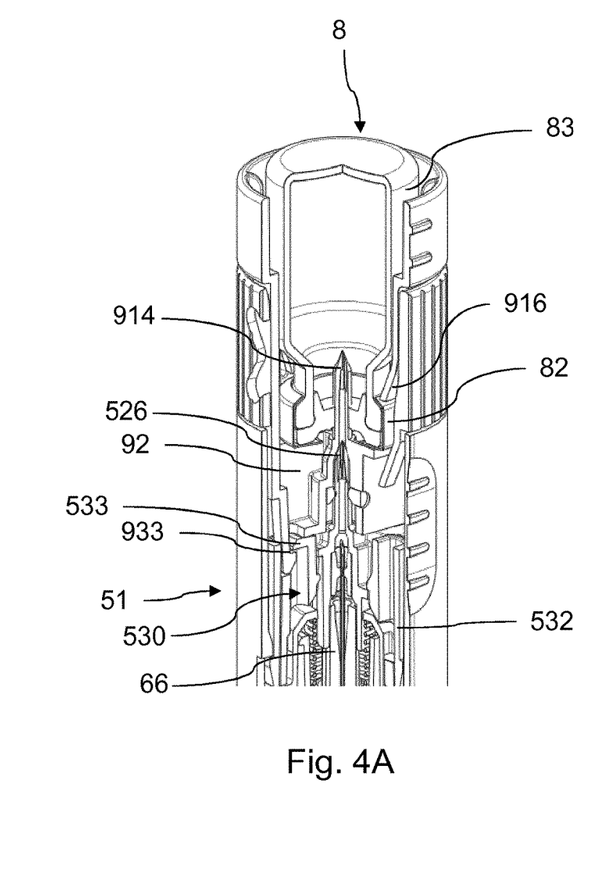
FIG. 4A shows a detail of a further partially sectioned view of the medical delivery device of FIG. 4, particularly highlighting an activation of the lock mechanism of the medical delivery device to allow a dosage from the first container lodged in the adapter container seat.

FIGS. 4 and 4A show a configuration when the container adapter 9 has been forwarded into the container seat 53 of the medical delivery device 1, to activate a lock mechanism of the medical delivery device. In particular the abutting surfaces 932 of the unlock member 93 have contacted the respective push portions of stems 532, so that the blocking surfaces incorporated by the stems 532 disengage from grooves of the housing of the delivery device 1. In this configuration, the operation of the dosing mechanism is allowed and a dosage from the first container 8 lodged in the adapter container seat 91 is enabled.

Figure 5:
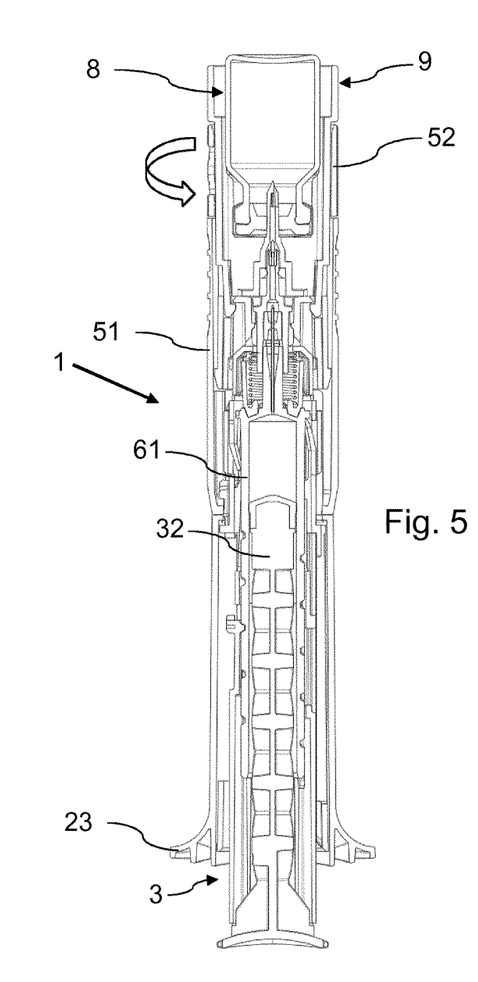
FIG. 5 shows a section view of the medical delivery device of FIG. 3, when the container adapter has brought the medical delivery device in an unlocked state and a liquid transfer from the first container to a dosage chamber of the medical delivery device is performed by rotation of a dial of a dosing mechanism of the medical delivery device.
Figure 5A:
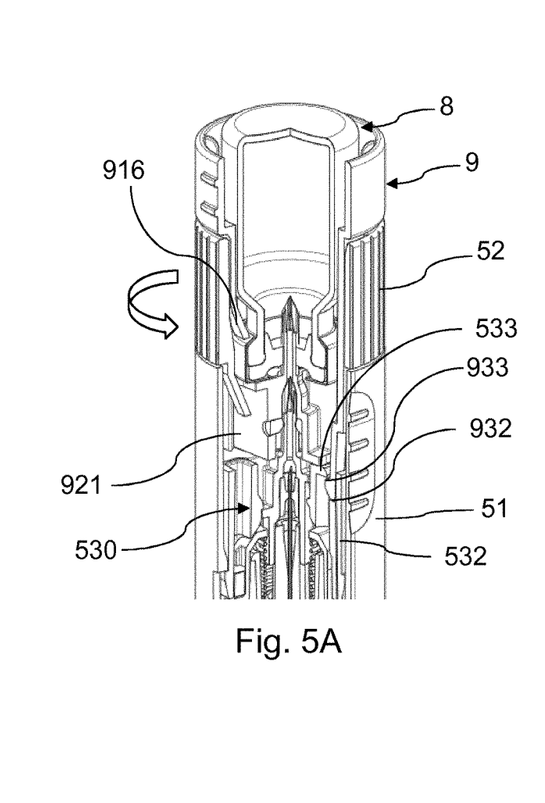
FIG. 5A shows a detail of a further partially sectioned view of the medical delivery device of FIG. 5, particularly representing the rotation of the dial of the medical delivery device in the unlocked state.

FIGS. 5 and 5A show that, after the container adapter 9 has brought the medical delivery device in an unlocked state, a liquid transfer from the first container 8 to a dosage chamber 61 of the medical delivery device is performed by rotation of a dial 52 of a dosing activator 5 of the medical delivery device 1.

Once the dosage from the first container 8 has been completed, the container adapter 9, together with the used first container 8, can be removed from the container seat 53 of the medical delivery device 1.

Figure 6:
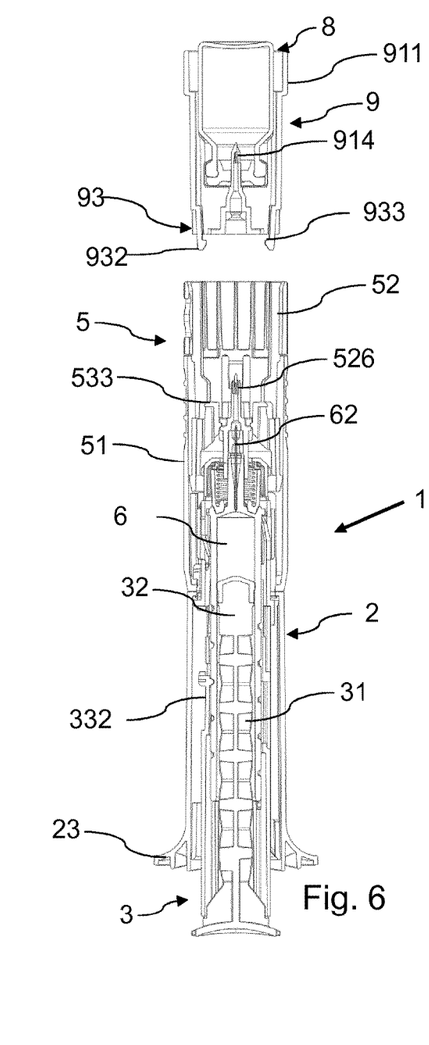
FIG. 6 shows a section view of the medical delivery device of FIG. 3, when the liquid transfer from the first container lodged in the container adapter to a dosage chamber of the medical delivery device has been completed and the container adapter is removed from a container seat of the medical delivery device together with the first container.
Figure 6A:
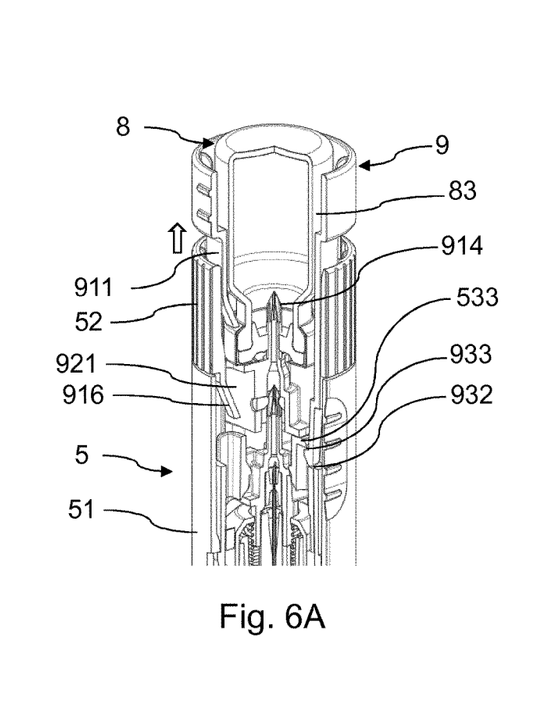
FIG. 6A shows a detail of a further partially sectioned view of the medical delivery device of FIG. 6, particularly representing the removal of the container adapter and the returning of the medical delivery device in a locked state wherein operation of the dosing mechanism is prevented.

In FIGS. 6 and 6A it is shown how, upon removal of the container adapter 9, the medical delivery device 1 returns in a locked state wherein operation of the dosing mechanism is prevented. This is achieved thanks to engaging surfaces 933 engaging behind a pull portion 533 of the lock mechanism when the container adapter is forwarded into the container seat 53. When the container adapter 9 is retracted from the medical delivery device 1, the unlock member 93 pulls the lock mechanism back, more specifically the pull portions 533 are axially displaced by the movement of the engaging surfaces 933. As a consequence, the blocking surfaces incorporated by the stems 532 engage back into the grooves of the housing 2 of the delivery device 1. Thus, the delivery device is brought into the locked state.

Figure 7:
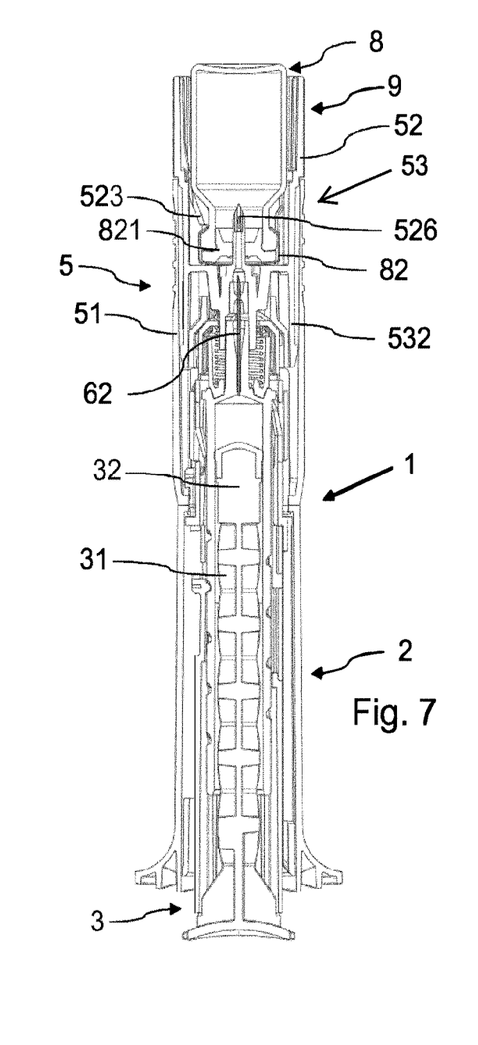
FIG. 7 shows a section view of the medical delivery device of FIG. 3, when the container adapter has been removed from the container seat of the medical delivery device and, conversely, a second container is directly positioned in the container seat of the medical delivery device.
Figure 7A:
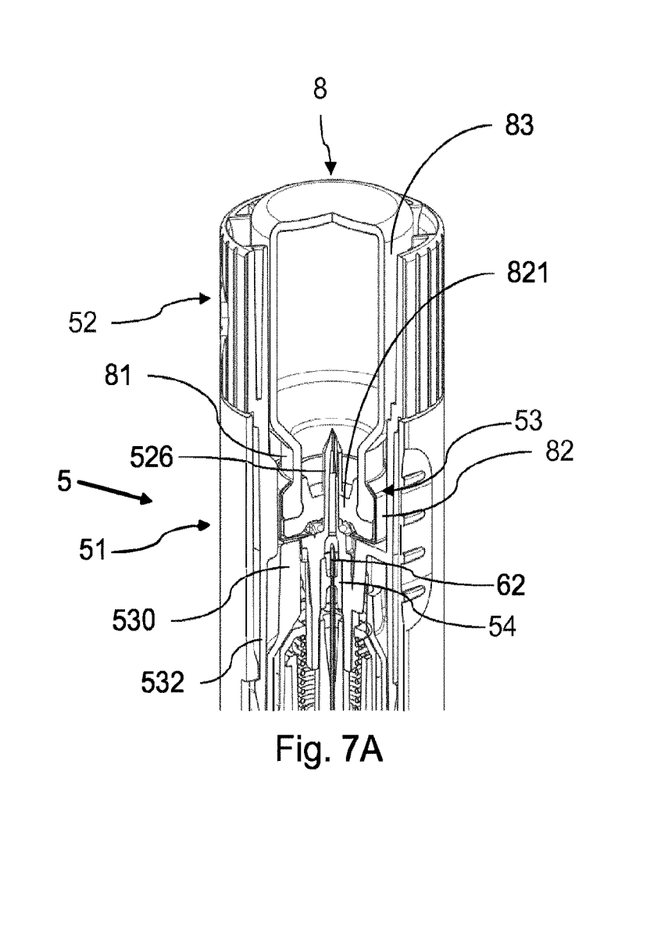
FIG. 7A shows a detail of a further partially sectioned view of the medical delivery device of FIG. 7, particularly representing the positioning of a second container in the container seat of the medical delivery device.

FIGS. 7 and 7A represent the positioning of a second container 8 directly in the container seat 53 of the medical delivery device 1, once the container adapter 9 has been removed from therein. In FIGS. 7 and 7A the locking mechanism is still in a configuration such that the dosing mechanism cannot be operated and rotation of the dial 52 is prevented. A securing element, for instance in the form of an adhesive strip stretching between the sleeve and the syringe body, can prevent accidental exposure of the needle 62 upon removal of the container adapter 9, contrasting possible ensuing dragging forces.

It has already been above described the functioning of the locking mechanism of the delivery device 1 in connection with the direct insertion in, or removal from, the container seat 53 of a container adapter together with a container 8 and the consequent axial displacement of the release member 530, respectively downwards in a distal direction or upwards in a proximal direction, to respectively disengage or engage the grooves of the housing 2.

In FIGS. 8 and 8A, the positioning of the second container 8 in the container seat 53 of the medical delivery device 1 has brought the medical delivery device 1 newly in an unlocked state, wherein withdrawing of a second liquid from the second container 8 into the dosage chamber 61 is enabled by rotation of the dial 52 of the dosing activator 5 of the medical delivery device 1.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A container adapter for a medical delivery device having a container seat for holding a container in a predefined position, a dosage chamber, a dosing mechanism to transfer a liquid from the container held in the container seat to the dosage chamber and a lock mechanism adapted to prevent operation of the dosing mechanism when no container is held in the container seat and to allow operation of the dosing mechanism when the container is held in the container seat, comprising:
   an adapter container seat arranged to hold the container in a predefined position:
   a joint structure arranged to be detachably positioned in the container seat of the medical delivery device and to connect the adapter container seat to the dosing mechanism of the medical delivery device when the joint structure is positioned in the container seat of the medical delivery device; and an unlock member adapted to activate the lock mechanism of the medical delivery device such that operation of the dosing mechanism is allowed when the joint structure is positioned in the container seat of the medical delivery device.

2. The container adapter of claim 1, wherein the unlock member comprises an abutting surface arranged to contact a push portion of the lock mechanism of the medical delivery device when the container adapter is forwarded into the container seat of the medical delivery device, such that the push portion of the lock mechanism is axially displaced when the container adapter is attached to the medical delivery device.

3. The container adapter of claim 1, wherein the unlock member comprises an engaging surface arranged to engage behind a pull portion of the lock mechanism of the medical delivery device when the container adapter is forwarded into the container seat of the medical delivery device, such that the pull portion of the lock mechanism is axially displaced when the container adapter is retracted from the medical delivery device.

4. The container adapter of claim 1, wherein the adapter container seat has a fixation structure adapted to irremovably hold the container in the predefined position.

5. The container adapter of claim 4, wherein the fixation structure of the adapter container seat preferably has a clip arranged to snap behind a head portion of the container when the container is held in the adapter container seat.

6. The container adapter of claim 1, comprising an alignment formation arranged to assure that the container adapter is in a predefined orientation relative to the medical delivery device when the joint structure is positioned in the container seat of the medical delivery device.

7. The container adapter of claim 1, wherein the joint structure is arranged to form an open tight duct between an interior of the container and the dosing mechanism of the medical delivery device when the container is held in the adapter container seat and the joint structure is positioned in the container seat of the medical delivery device.

8. The container adapter of claim 1, wherein the adapter container seat comprises a spike arranged to penetrate a cap of an opening of the container, when the container is held in the adapter container seat.

9. The container adapter of claim 8, wherein the spike of the adapter container seat extends in an interior of the adapter container seat.

10. The container adapter of claim 8, wherein the spike of the adapter container seat comprises a tip.

11. The container adapter of claim 10, wherein the spike of the adapter container seat comprises a conduit which runs from the tip longitudinally through the spike.

12. The container adapter of claim 1, further comprising a seal which seals the container seat of the medical delivery device to the joint structure, when the joint structure is positioned in the container seat of the medical delivery device.

13. The container adapter of claim 12, wherein the joint structure comprises a seal holder in which the seal is tightly arranged.

14. A delivery assembly, comprising:
a container adapter according to claim 1; and
a medical delivery device comprising a container seat for holding a container in a predefined position, a dosage chamber, a dosing mechanism to transfer a liquid from the container held in the container seat to the dosage chamber and a lock mechanism adapted to prevent operation of the dosing mechanism when no container is held in the container seat and to allow operation of the dosing mechanism when the container is held in the container seat.

15. The delivery assembly of claim 14, wherein the container seat of the medical delivery device has a fixation structure adapted to irremovably hold a container in a predefined position and the joint structure of the container adapter is arranged to prevent interaction with the fixation structure of the container seat of the medical delivery device, when the container adapter is held in the container seat of the medical delivery device.

16. The delivery assembly of claim 14, wherein the lock mechanism of the medical delivery device comprises a push portion and the unlock member of the container adapter comprises an abutting surface, the push portion of the lock mechanism and the abutting surface of the unlock member being arranged to interact when the container adapter is forwarded into the container seat of the medical delivery device, such that the push portion of the lock mechanism is axially displaced when the container adapter is attached to the medical delivery device.

17. The delivery assembly of claim 14, wherein the lock mechanism of the medical delivery device comprises a pull portion and the unlock member of the container adapter comprises an engaging surface, the pull portion of the lock mechanism and the engaging surface of the unlock member being arranged to inter-engage when the container adapter is forwarded into the container seat of the medical delivery device, such that the pull portion of the lock mechanism is axially displaced when the container adapter is retracted from the medical delivery device.

18. The delivery assembly of claim 14, comprising a securing element, wherein the container seat of the medical delivery device is decouplably mounted to a delivery orifice of the medical delivery device and the securing element is arranged for preventing unintended decoupling of the container seat from the delivery orifice, when the container adapter is retracted from the medical delivery device, wherein the securing element is a sheet piece having an adhering surface.

19. A method of delivering a liquid to a patient, comprising:
obtaining a first container with a liquid first mixing substance, a second container with a second mixing substance and the delivery assembly according to claim 14;
arranging the first container in the adapter container seat of the container adapter of the delivery assembly, positioning the joint structure of the container adapter of the delivery assembly in the container seat of the medical delivery device of the delivery assembly;
withdrawing the first substance from the first container into the dosage chamber of the medical delivery device of the delivery assembly;
retracting the container adapter of the delivery assembly from the medical delivery device of the delivery assembly;
positioning the second container in the container seat of the medical delivery device of the delivery assembly; and
withdrawing the second substance from the second container into the dosage chamber of the medical delivery device of the delivery assembly.

20. The method of claim 19, further comprising forwarding the first mixing substance into the second container when the second container is positioned in the container seat of the medical delivery device of the delivery assembly.

\* \* \* \* \*